(12) United States Patent
Pathak

(10) Patent No.: US 10,455,963 B2
(45) Date of Patent: Oct. 29, 2019

(54) SYSTEM AND METHOD FOR STABILIZING UNINTENTIONAL MUSCLE MOVEMENTS

(71) Applicant: Verily Life Sciences LLC, Mountain View, CA (US)

(72) Inventor: Anupam Pathak, Los Altos, CA (US)

(73) Assignee: Verily Life Sciences, LLC, South San Francisco, CA (US)

(*) Notice: Subject to any disclaimer, the term of this patent is extended or adjusted under 35 U.S.C. 154(b) by 0 days.

(21) Appl. No.: 16/124,898

(22) Filed: Sep. 7, 2018

(65) Prior Publication Data
US 2019/0000251 A1    Jan. 3, 2019

Related U.S. Application Data

(63) Continuation of application No. 13/250,000, filed on Sep. 30, 2011.

(51) Int. Cl.
*A61B 5/11* (2006.01)
*A61F 4/00* (2006.01)
(Continued)

(52) U.S. Cl.
CPC ............ *A47G 21/08* (2013.01); *A47G 21/02* (2013.01); *A61B 5/0022* (2013.01);
(Continued)

(58) Field of Classification Search
CPC ................................. A61B 5/1101; A62F 4/00
See application file for complete search history.

(56) References Cited

U.S. PATENT DOCUMENTS 3,711,638 A    1/1973    Davies
4,479,797 A    10/1984   Kobayashi et al.
(Continued)

FOREIGN PATENT DOCUMENTS

AT    411 011 B       9/2003
CN    203646979 U     6/2014
(Continued)

OTHER PUBLICATIONS

Smaga, S., "Tremor," American Family Physician 68(8):1545-1552, Oct. 2003.
(Continued)

*Primary Examiner* — Bruce E Snow
*Assistant Examiner* — Melissa A Hoban
(74) *Attorney, Agent, or Firm* — Christensen O'Connor Johnson Kindness PLLC

(57) ABSTRACT

A handheld system includes a motion-generating mechanism having a first motor mounted to a housing to generate a first rotary motion and a second motor coupled to a first output of the first motor such that the first rotary motion imparts to the second motor and rotates the second motor within the housing. The second motor generates a second rotary motion. An attachment arm extends out of the housing and has a first end coupled to a second output of the second motor and a second end configured to attach a user assistive device. A motion sensor senses a motion of the handheld system and generates a signal in response. A control system is coupled to receive the signal and to control the first and second rotary motions with commands generated based at least in part upon the signal. The commands direct the motion-generating mechanism to stabilize unintentional muscle movements.

20 Claims, 5 Drawing Sheets

(51) Int. Cl.
*A47G 21/08* (2006.01)
*A47G 21/02* (2006.01)
*A61B 5/00* (2006.01)
*G06F 19/00* (2018.01)
*G16H 40/67* (2018.01)
*A61F 2/08* (2006.01)

(52) U.S. Cl.
CPC .......... *A61B 5/1101* (2013.01); *A61B 5/6887* (2013.01); *A61F 4/00* (2013.01); *G06F 19/00* (2013.01); *G16H 40/67* (2018.01); *A47G 2200/046* (2013.01); *A61B 2562/0219* (2013.01); *A61F 2/08* (2013.01)

(56) References Cited

U.S. PATENT DOCUMENTS

| | | |
|---|---|---|
| 4,766,708 A | 8/1988 | Sing |
| 5,148,715 A | 9/1992 | Blaser et al. |
| 5,316,479 A | 5/1994 | Wong et al. |
| 5,562,707 A | 10/1996 | Prochazka et al. |
| 5,691,898 A | 11/1997 | Rosenberg et al. |
| 5,934,250 A | 8/1999 | Fujikawa et al. |
| 6,234,045 B1 | 5/2001 | Kaiser |
| 6,238,384 B1 | 5/2001 | Peer |
| 6,458,089 B1 | 10/2002 | Ziv-Av |
| 6,547,782 B1 | 4/2003 | Taylor |
| 6,695,794 B2 | 2/2004 | Kaiser et al. |
| 6,697,048 B2 | 2/2004 | Rosenberg et al. |
| 6,697,748 B1 | 2/2004 | Rosenberg et al. |
| 6,704,001 B1 | 3/2004 | Schena et al. |
| 6,704,002 B1 | 3/2004 | Martin et al. |
| 6,730,049 B2 | 5/2004 | Kalvert |
| 6,740,123 B2 | 5/2004 | Davalli et al. |
| 6,743,187 B2 | 6/2004 | Solomon et al. |
| 6,946,812 B1 | 9/2005 | Martin et al. |
| 7,106,313 B2 | 9/2006 | Schena et al. |
| 7,224,642 B1 | 5/2007 | Tran |
| 7,725,175 B2 | 5/2010 | Koeneman et al. |
| 7,883,479 B1 | 2/2011 | Stanley et al. |
| 8,286,723 B2 | 10/2012 | Puzio et al. |
| 8,308,664 B2 | 11/2012 | Pathak et al. |
| 9,074,847 B1 | 7/2015 | Sullivan et al. |
| 2001/0012932 A1 | 8/2001 | Peer |
| 2003/0006357 A1 | 1/2003 | Kaiser et al. |
| 2003/0036805 A1 | 2/2003 | Senior |
| 2003/0209678 A1 | 11/2003 | Pease |
| 2005/0113652 A1 | 5/2005 | Stark et al. |
| 2006/0044942 A1 | 3/2006 | Brinn et al. |
| 2006/0241510 A1 | 10/2006 | Halperin et al. |
| 2007/0050139 A1 | 3/2007 | Sidman |
| 2007/0109783 A1 | 5/2007 | Wilson et al. |
| 2007/0270784 A1 | 11/2007 | Smith et al. |
| 2009/0031839 A1 | 2/2009 | Shimizu et al. |
| 2009/0173351 A1 | 7/2009 | Sahin et al. |
| 2009/0203972 A1 | 8/2009 | Heneghan et al. |
| 2009/0227925 A1 | 9/2009 | McBean et al. |
| 2009/0254003 A1 | 10/2009 | Buckman |
| 2009/0276058 A1 | 11/2009 | Ueda et al. |
| 2010/0013860 A1 | 1/2010 | Mandella et al. |
| 2010/0036384 A1 | 2/2010 | Gorek et al. |
| 2010/0079101 A1 | 4/2010 | Sidman |
| 2010/0130873 A1 | 5/2010 | Yuen et al. |
| 2010/0198362 A1 | 8/2010 | Puchhammer |
| 2010/0228362 A1 | 9/2010 | Pathak et al. |
| 2010/0274365 A1 | 10/2010 | Evans et al. |
| 2011/0112442 A1 | 5/2011 | Meger et al. |
| 2012/0139456 A1 | 6/2012 | Takano et al. |
| 2012/0249310 A1 | 10/2012 | Hotaling |
| 2013/0060124 A1 | 3/2013 | Zietsma |
| 2013/0060278 A1 | 3/2013 | Bozung et al. |
| 2013/0118320 A1 | 5/2013 | Richardson |
| 2013/0123666 A1 | 5/2013 | Giuffrida et al. |
| 2013/0123684 A1 | 5/2013 | Giuffrida et al. |
| 2013/0123759 A1 | 5/2013 | Kang et al. |
| 2013/0297022 A1 | 11/2013 | Pathak |
| 2014/0171834 A1 | 6/2014 | DeGoede et al. |
| 2014/0257047 A1 | 9/2014 | Sillay et al. |
| 2014/0257141 A1 | 9/2014 | Giuffrida et al. |
| 2014/0303605 A1 | 10/2014 | Boyden et al. |
| 2014/0303660 A1 | 10/2014 | Boyden et al. |

FOREIGN PATENT DOCUMENTS

| | | |
|---|---|---|
| JP | 2008-067936 A | 3/2008 |
| JP | 2010-118798 A | 5/2010 |
| WO | 00/78263 A2 | 12/2000 |
| WO | 2008/123200 A1 | 10/2008 |
| WO | 2014/113813 A1 | 7/2014 |
| WO | 2015/003133 A1 | 1/2015 |

OTHER PUBLICATIONS

Third Office Action, dated Feb. 26, 2016, in Chinese Application No. 201280047035X, 8 pages.
Umemura, A., et al., "Deep Brain Stimulation for Movement Disorders: Morbidity and Mortality in 109 Patients," Journal of Neurosurgery 98:779-784, 2003.
Wireless & Mobile Human Monitoring, Latency Tech Note—Wireless Physiological Monitoring, Motion Sensor Latencies for Software Development, <http://glneurotech.com/bioradio/latency-tech-note> [retrieved Feb. 3, 2015], 4 pages.
Wireless & Mobile Human Monitoring, wireless motion sensor for 30 data acquisition via Bluetooth technology, Wireless Motion Sensor, <http://glneurotech.com/bioradio/physiological-signal-monitoring/wireless-motion-sensor> [retrieved Feb. 3, 2015], 3 pages.
Anouti, A., et al., "Tremor Disorders Diagnosis and Management," Western Journal of Medicine 162(6):510-513, 1995.
Australian Examination Report, dated Jul. 24, 2014, in Australian Application No. 2012316278, 3 pages.
Australian Notice of Acceptance, dated Jan. 15, 2015, in Australian Application No. 2012316278, 2 pages.
Australian Notice of Grant, dated May 14, 2015, in Australian Application No. 2012316278, 2 pages.
Bertacchini, O.W., et al., "Fatigue Life Characterization of Shape Memory Alloys Undergoing Thermomechanical Cyclic Loading," Smart Structures and Materials 5053:612-624, 2003.
Brin, M.F., and W. Koller, "Epidemiology and Genetics of Essential Tremor," Movement Disorders 13(S3):55-63, 1998.
Canadian Office Action dated Oct. 10, 2017, issued in Canadian Application No. 2,850,138, 3 pages.
Cao, C., et al., "Robotics in Healthcare: HF Issues in Surgery," 2007, <http://fase.tufts.edu/mechanical/EREL/Publications/D-4.pdf>, 33 pages.
DC-Micromotors, Application Datasheet, 0615 4.5S, 2010, <http://www.micromo.com>.
Deuschl, G., et al., "Treatment of Patients With Essential Tremor," Lancet Neurology 10(2):148-161, Feb. 2011.
Diamond, A., et al., "The Effect of Deep Brain Stimulation on Quality of Life in Movement Disorders," Journal of Neurology, Neurosurgery & Psychiatry 76(9):1188-1193, Sep. 2005.
Elble, R.J., et al., "Essential Tremor Frequency Decreases With Time," Neurology 55(10):1547-1551, 2000.
Elble, R.J., "Physiologic and Essential Tremor," Neurology 36(2):225-231, 1986.
European Search Report, dated Jun. 10, 2015, in European Application No. 12834632.7, 5 pages.
First Chinese Office Action, dated Apr. 28, 2015, in Chinese Application No. 2012-80047035.X, 10 pages.
First Japanese Office Action, dated Mar. 31, 2015, in Japanese Application No. 2014-533640, 5 pages.
First Office Action, dated Aug. 20, 2015, in Korean Application No. 10-2014-7011131, 7 pages.
Great Lakes Neurotechnologies, "Great Lakes Neurotechnologies Awarded Patent for Sensor Based Continuous Parkinsons Assessment During Daily Activities," Press Release, <www.glneurotech.com>, Dec. 3, 2013, 2 pages.

(56) References Cited

OTHER PUBLICATIONS

Heath, M., et al., "Design Considerations in Active Orthoses for Tremor Suppression: Ergonomic Aspects and Integration of Enabling Technologies," Proceedings of the AAATE 2003 Conference—Assistive Technology—Shaping the Future, Dublin, Ireland, Aug. 30-Sep. 3, 2003, pp. 842-846.
International Preliminary Report on Patentability, dated Apr. 1, 2014, in International Application No. PCT/US2012/057048, 5 pages.
International Preliminary Report on Patentability, dated Jan. 14, 2016, in International Application No. PCT/US2014/045409, 8 pages.
International Search Report and Written Opinion dated Dec. 17, 2012, in International Application No. PCT/US2012/057048.
International Search Report and Written Opinion of the International Searching Authority, dated Jul. 1, 2015, in International Application No. PCT/US2015/025781.
International Search Report and Written Opinion of the International Searching Authority, dated Nov. 3, 2014, in International Application No. PCT/US2014/045409, 9 pages.
International Search Report and Written Opinion, dated Apr. 6, 2016, in International Application No. PCT/US2016/013704, 19 pages.
Japanese Office Action dated Jan. 10, 2017, in Japanese Application No. 2016-000701, 15 pages.
Japanese Office Action dated Apr. 13, 2017, issued in Japanese Application No. 2016-000701, 13 pages.
Korean Office Action dated Aug. 25, 2017, issued in Korean Application No. 10-2016-7010282, 9 pages.
Kostikis, N., et al., "Smartphone-Based Evalution of Parkinsonian Hand Tremor: Quantitative Measurements vs Clinical Assessment Scores," Proceedings of the 36th Annual International Conference of the IEEE Engineering in Medicine and Biology Society, Aug. 25, 2014, pp. 906-909.
Louis, E.D., "Essential Tremor," Handbook of Clinical Neurology 100:433-448, Jan. 2011.
Louis, E.D., et al.,"Correlates of Functional Disability in Essential Tremor," Movement Disorders 16(5):914-920, 2001.
Louis, E.D., et al., "How Common is the Most Common Adult Movement Disorder? Estimates of the Prevalence of Essential Tremor Throughout the World," Movement Disorders 13(1):5-10, 1998.
Manto, M., et al., "Dynamically Responsive Intervention for Tremor Suppression," IEEE Engineering in Medicine and Biology 22(3):120-132, 2003.
Meshack, R.P., et al., "A Randomized Controlled Trial of the Effects of Weights on Amplitude and Frequency of Postural Hand Tremor in People With Parkinson's Disease," Clinical Rehabilitation 16(5):481-492, 2002.
National Parkinson Foundation, "Treatment Options," 2009, <http://www.parkinson.org/Parkinson-s-Disease/Treatment>.
Non-Final Office Action, dated Apr. 6, 2017, in U.S. Appl. No. 13/935,387, 14 pages.
Non-Final Office Action, dated Apr. 11, 2016, in U.S. Appl. No. 13/935,387, 13 pages.
Non-Final Office Action, dated Apr. 3, 2015, in U.S. Appl. No. 13/935,387, 25 pages.
Notice of Allowance, dated Dec. 2, 2014, in Japanese Application No. 2014-533640, 3 pages.
Pathak, A., et al. "Dynamic Characterization and Single-Frequency Cancellation Performance of SMASH (SMA actuated stabilizing handgrip)," in "Modeling, Signal Processing, and Control for Smart Structures," Proceedings of SPIE 6926:692602-1-692602-12, 2008.
Pathak, A., et al., "Handheld Tool for Leveling Uncoordinated Motion," U.S. Appl. No. 14/668,516, filed Mar. 25, 2015.
Pathak, A., et al., "Measurement and Collection of Human Tremors Through a Handheld Tool," U.S. Appl. No. 14/627,893, filed Feb. 20, 2015.
Pathak, A., et al., "A Noninvasive Handheld Assistive Device to Accommodate Essential Tremor: A Pilot Study," Brief Report, Movement Disorders 29(6):838-842. May 2014.
Pedley, M., "Tilt Sensing Using a Three-Axis Accelerometer," Freescale Semiconductor, Inc., Application Note, Document No. AN3461, Rev. 6, Mar. 2013, 22 pages.
Riviere, C.N., et al., "Toward Active Tremor Canceling in Handheld Microsurgical Instruments," IEEE Transactions on Robotics and Automation 19(5):793-800, Oct. 2003.
Rocon, E., et al., "Mechanical Suppression of Essential Tremor," The Cerebellum 6(1):73-78, 2007.
Rocon, E., et al., "Rehabilitation Robotics: A Wearable Exo-Skeleton for Tremor Assessment and Suppression," Proceedings of the 2005 IEEE International Conference on Robotics and Automation, Barcelona, Apr. 18-22, 2005, pp. 2271-2276.
Rocon, E., et al., "Theoretical Control Discussion on Tremor Suppression via Biomechanical Loading," Proceedings of the AAATE 2003 Conference—Assistive Technology—Shaping the Future, Dublin, Ireland, Aug. 30-Sep. 3, 2003, pp. 832-836.
Second Chinese Office Action, dated Sep. 14, 2015, in Chinese Application No. 2012-80047035.X, 11 pages.
Shaw, J.A., and C.B. Churchill, "A Reduced-Order Thermomechanical Model and Analytical Solution for Uniaxial Shape Memory Alloy Wire Actuators," Smart Materials and Structures 18(6), 065001, Jun. 2009, 21 pages; entire document, especially Fig. 1b; p. 3, col. 1.
First Office Action for Chinese Patent Application No. 201610721118.2, dated Aug. 31, 2018, 19 pages.
Second Office Action mailed for Chinese Patent Application No. 201610721118.2, dated Apr. 4, 2019, 13 pages.

SYSTEM AND METHOD FOR STABILIZING UNINTENTIONAL MUSCLE MOVEMENTS

CROSS-REFERENCE TO RELATED APPLICATION

This application is a continuation application of U.S. patent application Ser. No. 13/250,000, filed on Sep. 30, 2011, the contents of which are incorporated herein by reference.

GOVERNMENT RIGHTS

This invention was made with Government support under grant No. NS070438 awarded by the National Institutes of Health (NIH). The Government has certain rights in the invention.

FIELD OF THE INVENTION

The present invention relates generally to unintentional muscle movements of a body, and more particularly, to a system and method for stabilizing the effects of these unintentional muscle movements.

BACKGROUND

Unintentional muscle movements of the human body, or human tremors, can occur in individuals suffering from neurological motion disorders including but not limited to Parkinson's Disease (PD) and Essential Tremor (ET). ET is the most common neurological motion disorder affecting as many as 10 million individuals in the United States and 270 million individuals worldwide. Due to the debilitating muscle movements associated with this disease, individuals with ET have difficulty in performing many daily functions such as eating and drinking. As a result, these individuals often suffer from social isolation, depression/anxiety, and an overall reduced Health Related Quality of Life (HRQoL).

Unintentional muscle movements of the human body can also occur in healthy individuals. These unintentional muscle movements are often exacerbated by environmental factors and situations that lead to fatigue, stress, nervousness, etc. For example, a military serviceperson may experience unintentional muscle movements while performing a surgical operation on the battlefield due to stress and nervousness and this may result in decreased performance.

For individuals suffering from neurological motion disorders, a variety of treatment options exist. Pharmacological treatments vary in effectiveness, can lead to severe side effects and are unable to slow or stop disease progression. Surgical procedures, such as Thalamotomy and thalamic Deep Brain Stimulation (DBS) can be expensive, dangerous, and limited in availability. Non-invasive solutions, such as physically grounded tremor suppression devices, physically force a person's tremor to cease but require complex and costly structures, cause user discomfort and cannot differentiate between intended and unintended movements.

These issues limit the adoption of these treatments to select neurological motion disorder cases. Also, these treatments are often not available for healthy individuals suffering from human tremor. Thus, for the majority of individuals that suffer from human tremor, there is a strong need for a non-invasive solution that overcomes the above issues. The present invention addresses such a need.

SUMMARY OF THE INVENTION

A system and method for stabilizing a position of an object are disclosed. In a first aspect, the system comprises a housing. The housing includes a subsystem. The system also includes an attachment arm coupled to the housing. At least one first sensor is placed along the attachment arm, wherein the attachment arm is configured to receive the object thereto. In response to an unintentional muscle movement by a user that adversely affects the motion of the object, the subsystem stabilizes the position of the object.

In a second aspect, the method comprises providing a subsystem within a housing and coupling an attachment arm to the housing. The method also includes placing at least one first sensor along the attachment arm, wherein the attachment arm is configured to receive the object thereto. In response to an unintentional muscle movement by a user that adversely affects the motion of the object, the subsystem stabilizes the position of the object.

BRIEF DESCRIPTION OF THE DRAWINGS

The accompanying drawings illustrate several embodiments of the invention and, together with the description, serve to explain the principles of the invention. One of ordinary skill in the art readily recognizes that the particular embodiments illustrated in the drawings are merely exemplary, and are not intended to limit the scope of the present invention.

DETAILED DESCRIPTION OF PREFERRED EMBODIMENTS

The present invention relates generally to unintentional muscle movements in a body, and more particularly, to a system and method for stabilizing the effects of these unintentional muscle movements. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiments shown but is to be accorded the widest scope consistent with the principles and features described herein.

Figure 1:
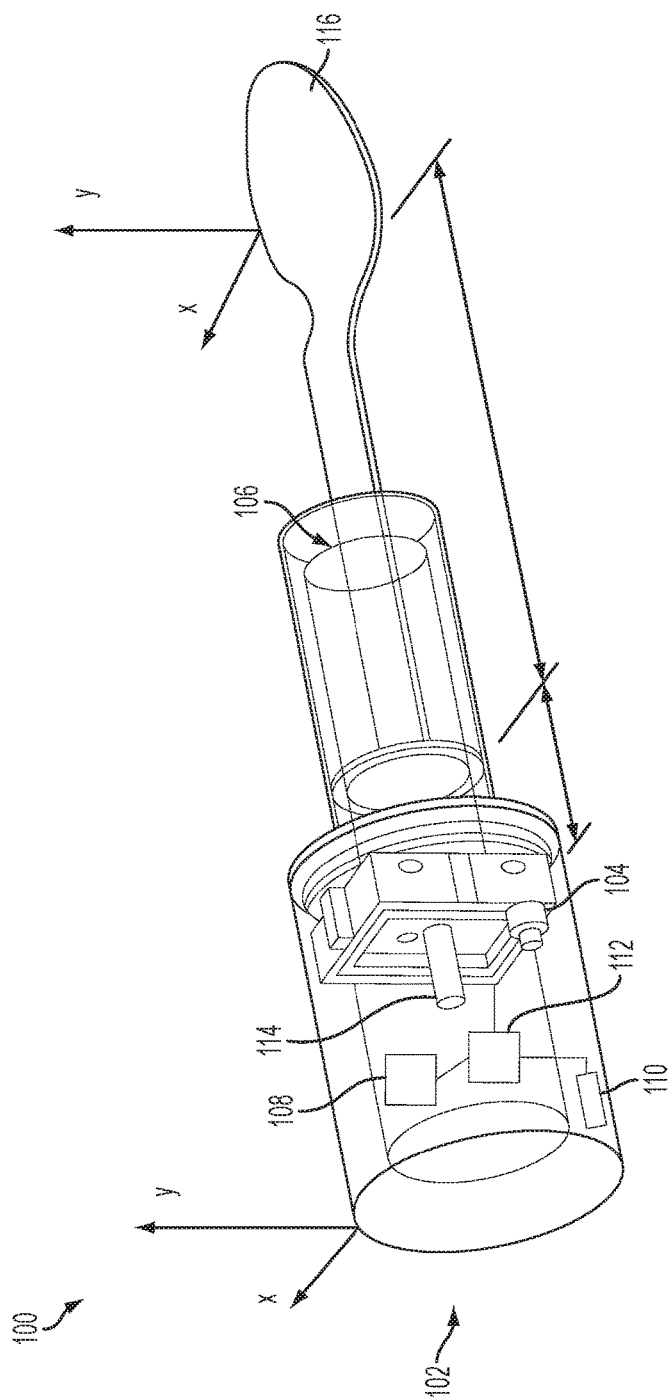
FIG. 1 illustrates a conventional handheld system that detects and compensates for unintentional muscle movements.

FIG. 1 illustrates a conventional handheld system 100 that detects and compensates for unintentional muscle movements. The handheld system 100 includes a base 102, a gripping element 106 coupled to the base 102, and an object 116 (in this embodiment, a spoon) coupled to the gripping element 106. The base 102 houses a stabilizing assembly using shape memory alloy (SMA) wires 104, a power source 108 coupled to the stabilizing assembly 104, a single sensor 110 coupled to the power source 108, a controller 112 coupled to the single sensor 110, and a shaft 114 coupled to the stabilizing assembly 104. SMA wires are alloy wires that, after deformation, undergo a phase change to return to their original cold-forged shape after sufficient heat is applied. The SMA wires utilized in the stabilizing assembly 104 are heated by the power source 108 to trigger this phase change.

In the handheld system 100, the single sensor 110 is located within the base 102 to detect a user's motion and then the sensor 110 commands the stabilizing assembly using SMA wires 104 to produce a canceling motion. Unfortunately, several problems exist preventing the immediate use of SMA wires. For example, SMA wires have not been proven for long-term, reliable use and also require significant complexity and cost to provide sufficient motion to cancel large amplitude (1-4 cm) disabling tremors.

In addition, because the single sensor 110 is located within the base 102, the use of the device is restricted to an object 116 that has a pre-determined length and weight that must be pre-programmed into the controller 112. Deviations from this pre-determined length or weight will result in control instabilities and a reduction in the efficacy of the motion cancellation.

A system and method in accordance with the present invention addresses these drawbacks. The system and method include an inertial sensor placed along an attachment arm and a motion-generating mechanism that does not utilize SMA wires. In so doing, the motion of the varying stabilized objects can be directly measured and there is no need for pre-programming the pre-determined lengths and weights into the controller. Additionally, a higher performing handheld form-factor solution is achieved and the size and cost of the active cancellation system is further reduced. To describe the features of the present invention in more detail, refer now to the following description in conjunction with the accompanying Figures.

Figure 2:
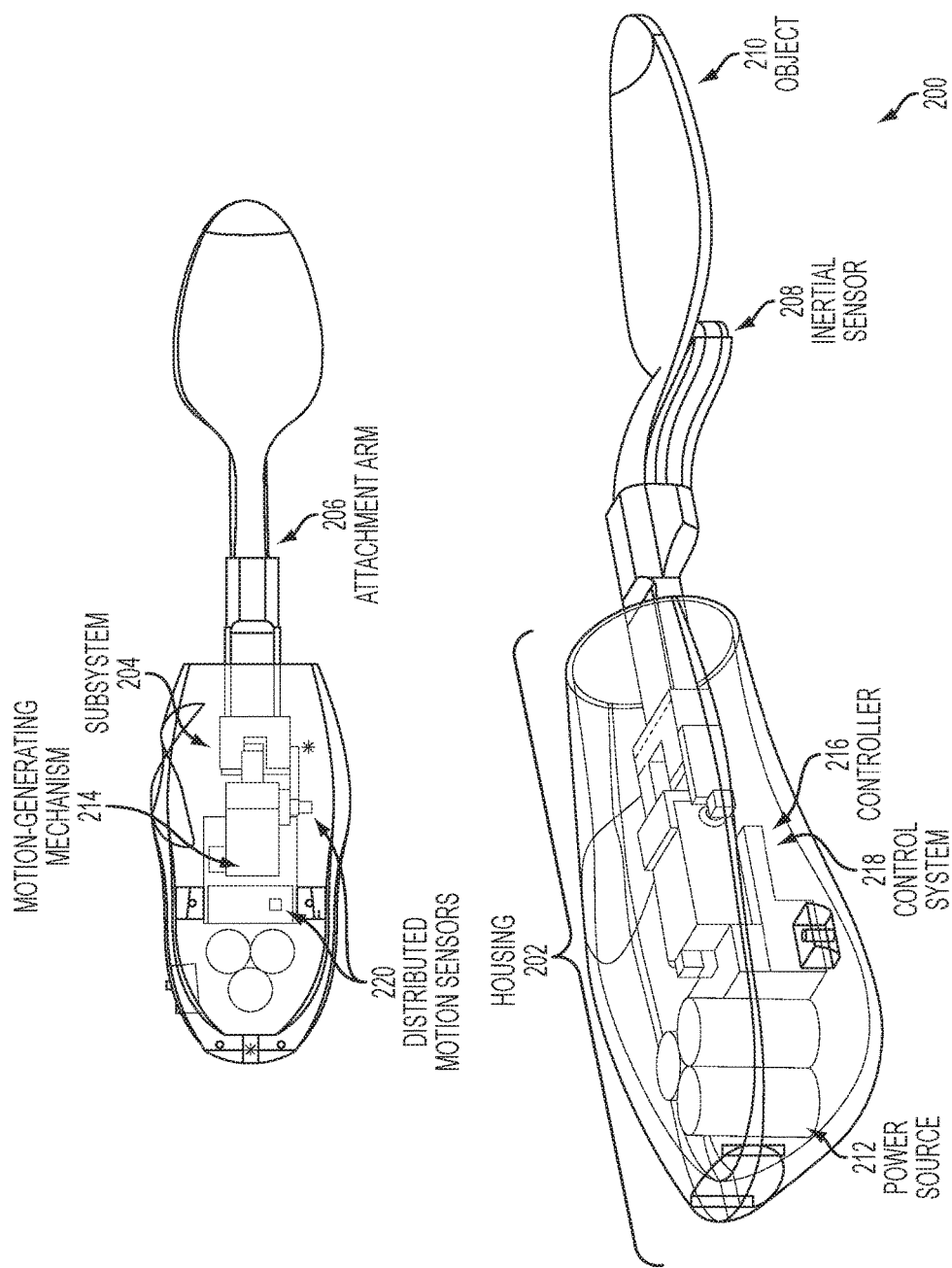
FIG. 2 illustrates a system that detects and compensates for unintentional muscle movements in accordance with an embodiment.

System Overview:

FIG. 2 illustrates a system 200 that detects and compensates for unintentional muscle movements in accordance with an embodiment. The system 200 includes a housing 202. The housing 202 includes a subsystem 204. The system 200 also includes an attachment arm 206 coupled to the housing 202. At least one inertial sensor 208 is placed along the attachment arm 206. The attachment arm 206 is configured to accept an object 210 thereto. The subsystem 204 further includes a portable power source 212, a motion-generating mechanism 214, a controller 216, a control system 218, and at least one distributed motion sensor 220.

The attachment arm 206 can receive the object 210 in a variety of ways including but not limited to a friction, snap, or other form of locking mechanism. The portable power source 212 may utilize a variety of options including but not limited to a rechargeable battery and a solar panel. The operation and details of the elements of the at least one inertial sensor 208, at least one distributed motion sensor 220, motion-generating mechanism 214, controller 216, and control system 218 will be described in more detail hereinafter.

The at least one inertial sensor 208 and the at least one distributed motion sensor 220 detect unintentional muscle movements and measure signals related to these unintentional muscle movements that are created when a user adversely affects motion of the object 210. These sensors also detect the motion of the stabilized output relative to the housing 202. The control system 218 sends voltage commands in response to the signals to the motion-generating mechanism 214 through the controller 216 to cancel the user's tremors or unintentional muscle movements. This cancellation maintains and stabilizes a position of the object 210, keeping it centered relative to the housing 202.

One of ordinary skill in the art readily recognizes that a system and method in accordance with the present invention may utilize various implementations of the controller 216, at least one inertial sensor 208, at least one distributed motion sensor 220, and control system 218 and that would be within the spirit and scope of the present invention. In one embodiment, the controller 216 comprises an electrical system capable of producing an electrical response from sensor inputs such as a programmable microcontroller or a field-programmable gate array (FPGA). In one embodiment, the controller 216 comprises an 8-bit ATMEGA8A programmable microcontroller manufactured by Atmel due to its overall low-cost, low-power consumption and ability to be utilized in high-volume applications.

In one embodiment, the at least one inertial sensor 208 is a sensor including but not limited to an accelerometer, gyroscope, or combination of the two. In one embodiment, the at least one distributed motion sensor 220 is a contactless position sensor including but not limited to a hall-effect magnetic sensor. In one embodiment, the control system 218 is a closed-loop control system.

The closed-loop control system senses motion and acceleration at various points in the system 200 and feeds detailed information into a control algorithm that moves the motion-generating mechanism 214 appropriately to cancel the net effect of a user's unintentional muscle movements and thus stabilize the position of the object 210. The operation and details of the elements of the control system and control algorithm will be described in more detail hereinafter.

Also, one of ordinary skill in the art readily recognizes that a system and method in accordance with the present invention may utilize a variety of objects including but not limited to kitchen utensils such as spoons and forks, grooming utensils such as make-up applicators, and various tools such as manufacturing, surgical and military tools. Thus, the system and method will be useful in not only improving the quality of life for the multitudes of individuals suffering from neurological motion disorders, but also in assisting in a variety of applications where physiological tremor is an issue including but not limited to manufacturing, surgical and military applications.

The system 200 stabilizes the object 210's position about a neutral position (selected to be θ=0) using the at least one inertial sensor 208. To achieve this, the position of the object 210 must be sensed along with the angle θ. For this position sensing, the at least one inertial sensor 208 is placed along the attachment arm 206 and is used to measure the absolute motion of the object 210 while providing low noise and sufficient sensitivity for the application. The direct sensor placement of the at least one inertial sensor 208 along the attachment arm 206 gives a unique advantage to the system 200 as it is extremely robust and does not rely on inverse kinematics/dynamics which may change depending on usage. Thus, as aforementioned, a variety of objects can be used as the object 210 without the need to pre-determine and pre-program the length and weight of the object 210 into the controller 216.

The at least one distributed motion sensor 220 is located within the housing 202 which is located at the base of the system 200. The at least one distributed motion sensor 220 measures the relative motion of the attachment arm 206 relative to the housing 202, wherein the object 210 is kept at a center position relative to the housing 202. In one embodiment, the at least one distributed motion sensor 220 is at least one custom contactless hall-effect position sensor that provides angular feedback for the control system 218 and relies on a changing magnetic field that is dependent on the actuation angle.

The changing magnetic field is detected by a strategically placed integrated circuit (IC) located within the at least one distributed motion sensor 220, whose analog output is read by the controller 216, providing a completely non-contact angular detection that is capable of withstanding a large number of cycles. The at least one distributed motion sensor 220, with its contactless sensing methods, provides significantly enhanced reliability over traditional direct-contact sensing methods such as potentiometers that wear over time.

Proper actuator operation is also a key to the overall operation of the system 200. Actuator options include SMA wires, piezoelectrics, linear voice-coils and coreless motors. However, SMA wires, piezoelectrics and linear voice-coils suffer from various fundamental problems. For example, as noted in the "Fatigue Life characterization of shape memory alloys undergoing thermomechanical cyclic loading" article within the "Smart Structures and Materials" publication, SMA wires suffer from reliability issues where failures occur after $10^4$ to $10^5$ cycles with strain amplitudes between 8.3% and 4.4%, which would amount to only 200 days usage time. Piezoelectrics, while capable of longer cycle times, are fragile and expensive. In addition, they require high operating voltages and thus require relatively large and expensive drive electronics. Linear voice-coils operate at lower voltages but suffer from low force outputs and high costs.

The present invention addresses these drawbacks by using a combination of coreless micro-motors and miniature gear-reduction systems coupled to the coreless micro-motors using a coupling mechanism for the motion-generating mechanism 214. In volume, coreless micro-motors are inexpensive and provide up to 1000 hours of operation time. Significant force of up to 10 newtons (N) can also be produced with these coreless micro-motors at the required tremor frequency of 0-5 hertz (Hz) through the use of a low-cost miniature gear-reduction system, with a total weight of only 6.5 grams (g). Furthermore, the power drawn from this technology is extremely low, estimated at 0.5 watts (W).

The coreless micro-motors are not only capable of holding a maximum load of 50 g while requiring 0.3 W of power, but are also capable of holding the lighter average filled tablespoon load of 14 g while requiring a significantly lower 0.06 W of power. Thus, the coreless micro-motors are suitable in generating the required forces for the system 200.

Figure 3:
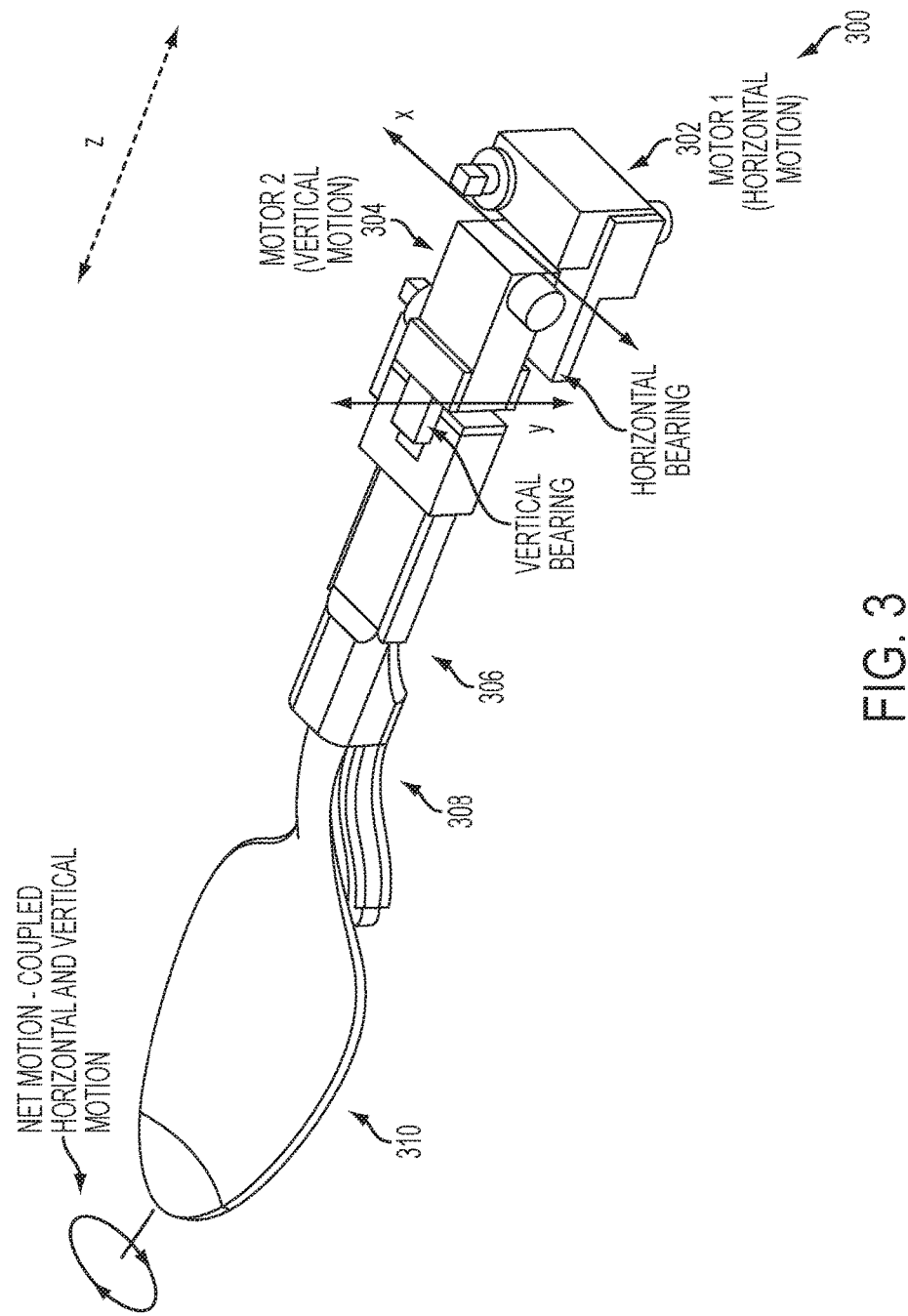
FIG. 3 illustrates a motion-generating mechanism in accordance with an embodiment.

FIG. 3 illustrates a motion-generating mechanism 300 in accordance with an embodiment. The motion-generating mechanism 300 includes a first miniature gear-reduction system coupled to a first coreless micro-motor 302 and a second miniature gear-reduction system coupled to a second coreless micro-motor 304. At least one inertial sensor 308 is placed along an attachment arm 306. The attachment arm 306 is configured to accept an object 310 thereto.

The first coreless micro-motor is capable of producing rotary motion in the horizontal (x) direction. This rotary motion is imparted to the second coreless micro-motor through a rigid connection that is supported by a horizontal bearing. The second coreless micro-motor is capable of producing motion in the vertical (y) direction. This motion from the second coreless micro-motor is supported by a vertical bearing.

A coupling mechanism is used to combine the horizontal and vertical motions of the two separate coreless micro-motor/miniature gear-reduction systems 302 and 304. This combination results in a bi-directional circular motion of the object 310 (in this embodiment, a spoon). One of ordinary skill in the art readily recognizes that a system and method in accordance with the present invention may utilize a variety of coupling mechanisms including but not limited to sliding bearing mechanisms, gimbal structures, or bellows structures and that would be within the spirit and scope of the present invention.

In the motion-generating mechanism 300, two degrees of freedom are generated from the two separate coreless micro-motor/miniature gear-reduction systems 302 and 304. Additional degrees of freedom (e.g., a third in the z-direction) can be added to the motion-generating mechanism 300 by adding motion to the output of the first coreless micro-motor or the output of the second coreless micro-motor.

Figure 4:
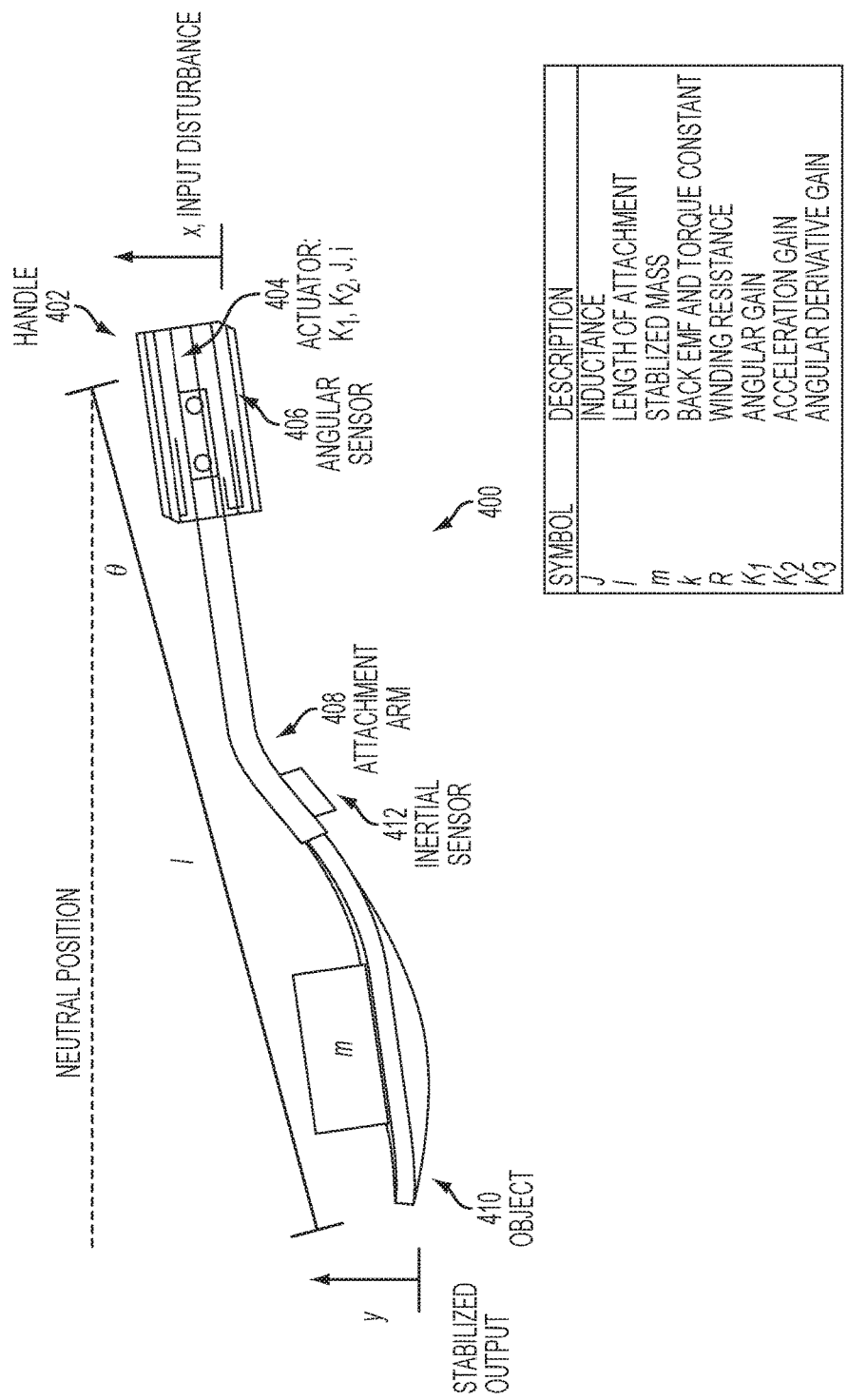
FIG. 4 illustrates an analytical model in accordance with an embodiment.

System Modeling:

To assist with the development of the control system type and parameter values, an analytical model of the system 200's properties was created. FIG. 4 illustrates an analytical model 400 in accordance with an embodiment. The analytical model 400 includes a handle 402, an actuator 404, an angular sensor 406, an attachment arm 408, an object 410, and an inertial sensor 412. The analytical model 400 was created with sufficient complexity to capture the dynamics of the system 200 and its response when synthesized with a closed-loop control system.

While the system 200 is designed to provide stabilization in multiple directions (e.g., vertical, horizontal, and the z-direction), analysis and modeling in only one direction is required because the motion outputs were symmetric and completely decoupled from one another. Thus, results from the vertical direction are directly applicable to other directions such as but not limited to the horizontal direction, assuming gravitational effects are negligible.

In the analytical model 400, the object 410 moves in the vertical y direction. The tremor disturbance or unintentional muscle movement (coordinate x) is assumed to act directly on the handle 402. The object 410 requiring stabilization (distance/from the base) moves a vertical distance y. This distance is related to the base coordinate x through the transformation, $$y = x + l\theta, \quad (1)$$

where small angles are assumed. The actuator 404 is capable of moving the object 410 through the angle θ based on the controller's voltage output. The output torque of the actuator 404's coreless motor T is proportional to its armature current i through the relationship $$T = K_t i, \quad (2)$$

where $K_t$ is a constant. Similarly, the back electromotive force (emf), e is related to the coreless motor's rotational velocity through $$e = K_e \dot{\theta}. \quad (3)$$

For simplicity, and based on the manufacturer's specifications, $K_e$ and $K_t$ are approximately equal and are therefore set to a constant k. With the actuator 404's model Equations 2 and 3, the system equations can be constructed through a combination of Newton's and Kirchhoff's laws. Through a moment balance the dynamic equation is constructed as $$I\ddot{\theta} + \frac{ml}{2}\ddot{x} = ki. \quad (4)$$

The second system equation is constructed as $$J\frac{di}{dt} + Ri = V - k\dot{\theta} \qquad (5)$$

where V is the input voltage/command signal from the controller, J is the inductance of the actuator 404, and R is the internal resistance of the actuator 404.

The system 200 acts as a low-pass filter because it is designed to cancel high-frequency tremor disturbances/unintentional muscle movements while retaining low-frequency intended motions. Thus, the system 200 can be modeled as a transfer function, where an input amplitude X (tremor disturbance) is entered into the system 200, and an output Y (motion of the stabilized object) is observed and controlled.

For further analysis on tremor cancellation and to assist in controller design, the system Equations 4 and 5 were transformed into the frequency domain and manipulated to produce the desired transfer function. Using the coordinate transformation Equation 1 and performing a Laplace transform, Equations 4 and 5 were modified to produce $$\frac{I}{l}s^2(Y(s) - X(s)) + \frac{ml}{2}s^2 X(s) = kI(s) \qquad (6)$$

and $$JsI(s) + RI(s) = V - \frac{Ks}{l}(Y(s) - X(s)). \qquad (7)$$

Solving Equation 7 for I(s) and substituting the result into Equation 6 produces a single equation $$\frac{I}{l}s^2(Y(s) - X(s)) + \frac{ml}{2}s^2 X(s) = k\left(\frac{V - \frac{Ks}{l}(Y(s) - X(s))}{Js + R}\right). \qquad (8)$$

The remaining input in Equation 8 is V, which is the input voltage/command signal from the controller. This signal was designed to be simple in nature to minimize computational requirements and thus significantly reduce the cost and power consumption of the necessary microcontroller.

Figure 5:
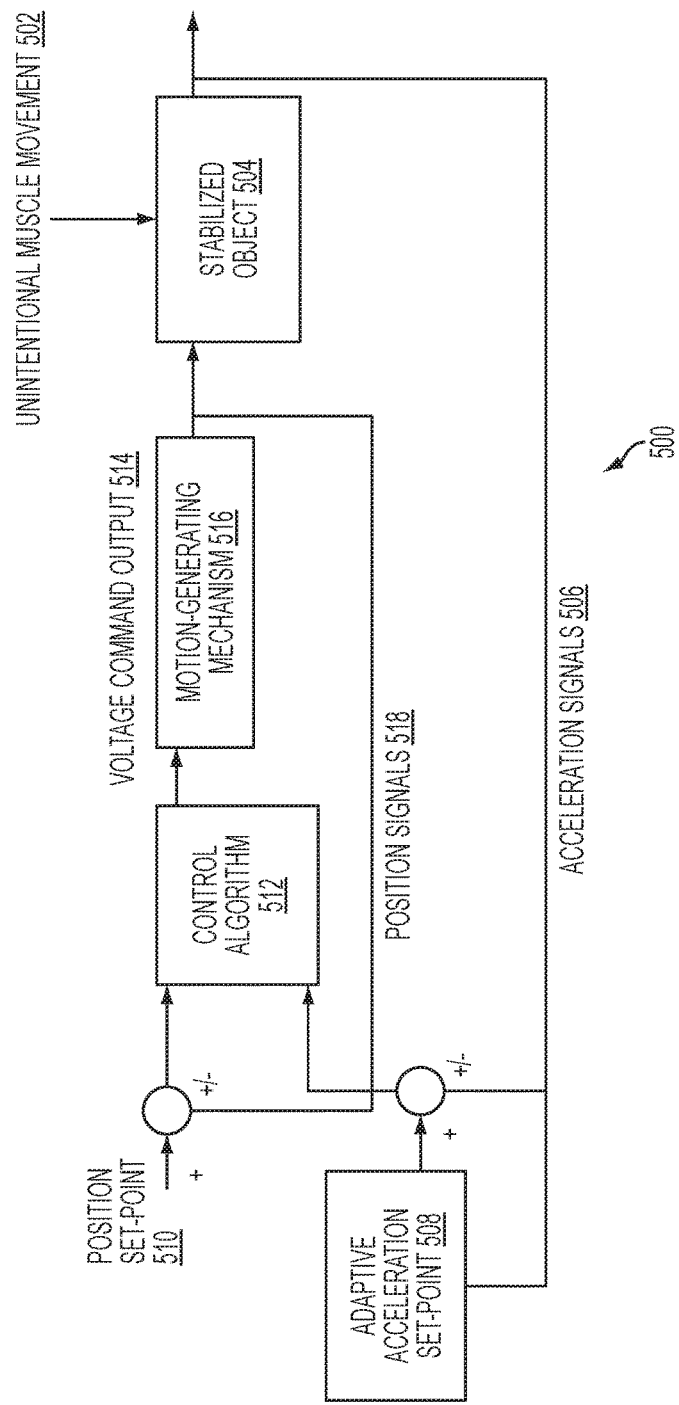
FIG. 5 illustrates a system diagram of the control system in accordance with an embodiment.

FIG. 5 illustrates a system diagram 500 of the control system 218 in accordance with an embodiment. The system diagram 500 includes an unintentional muscle movement 502, a stabilized object 504, acceleration signals 506, an adaptive acceleration set-point 508, a position set-point 510, a control algorithm 512, a voltage command output 514, a motion-generating mechanism 516, and position signals 518.

An unintentional muscle movement 502 by a user that adversely affects the motion of the stabilized object 504 is detected. Position signals 518 relative to the housing are measured by the at least one contactless position angular sensor and then are compared to the position set-point 510 that is stored in the microcontroller's memory (e.g., Electrically Erasable Programmable Read-Only Memory (EEPROM)). The position set-point 510 is the neutral position of the stabilized object 504 and is initially calibrated when the system 200 is first activated. This comparison results in a first input signal.

Acceleration signals 506 are measured by the at least one inertial sensor and then are compared to an adaptive acceleration set-point 508. The adaptive acceleration set-point 508 removes the effects of slow changes in the gravity field due to the changing orientation of the device. The adaptive acceleration set-point 508 can be implemented through the use of a median filter, low-pass filter, or other digital/analog filter capable of removing low frequencies from a signal. This comparison results in a second input signal.

The control algorithm 512 processes the first and second input signals and sends an appropriate voltage command output 514 to the motion-generating mechanism 516 in each controlled direction to actively cancel the user's unintentional muscle movement and maintain the stabilized object 504.

Based on these two input signals (acceleration signal and angle θ), a control law must be constructed for the control algorithm 512. One of ordinary skill in the art readily recognizes that a system and method in accordance with the present invention may utilize a variety of different control laws that provide tremor disturbance cancellation while ensuring stability of the object and that would be within the spirit and scope of the present invention.

For example, a control law can be derived by applying proportional and derivative gains to the angle θ along with the acceleration signal resulting in $$V = K_1\theta - K_2\ddot{x} + K_3\dot{\theta}. \qquad (9)$$

In this example, the feedback on the acceleration term provides the desired low-pass filtering properties. In the exemplified control law (Equation 9), the proportional feedback on the angle θ is applied to allow the device to mimic the function of conventional implements. This is achieved by creating "stiffness" in the angular direction to allow the device to support various loads and while remaining in the neutral position during the inactive state. Derivative control on the angular input was selected for stability, particularly to dampen any resonances introduced by the proportional feedback on θ. The exemplified control law is both effective and computationally simple.

This allows the control algorithm 512 to be implemented in the highly compact, low-power, and low-cost microcontrollers of the system 200. Substituting the exemplified control law (Equation 9) into V in Equation 8 and expanding the terms allows Equation 8 to be expressed as the following transfer function $$\frac{Y(s)}{X(s)} = \frac{n}{d} \qquad (10)$$

where the numerator is $$n = (2ILJ^2 - mL^3J^2)s^4 + (4ILJR - 2mL^3JR)s^3 + (2K^2LJ + 2K_3KLJ - mL^3R^2 + 2ILR^2)s^2 + (2K^2LR + 2K_1KLJ + 2K_3KLR)s + 2K_1KLR \qquad (11)$$

and the denominator is $$d = (2ILJ^2)s^4 + (2K_2KL^2J + 4ILJR)s^3 + (2K^2LJ + 2K_2KL^2R + 2K_3KLJ + 2ILR^2)s^2 + (2K^2LR + 2K_1KLJ + 2K_1KLR)s + 2K_1KLR. \qquad (12)$$

To reject unintentional muscle movements while retaining intended motions, the parameters of the exemplified control law (Equation 9) are optimized through numerical simulation. For example, this optimization minimizes the average displacement magnitude of the stabilized object 504 (Y, Equation 10) over the unintentional muscle movement frequency range of 3-7 Hz, while varying the controller gains $K_1$, $K_2$, $K_3$. Further, in this example, the constraints are defined such that low-frequency motions in the intended motion frequency range of 0-1 Hz are unaffected and stability is mathematically ensured. The average phase lag is also constrained to be less than 15 degrees from 0-1 Hz, which is assumed to be unnoticeable to the user.

For the optimization, computational functions are written to interact with the trust-region reflective optimization algorithm fmincon in Matlab. The algorithm is run to provide a final solution, K=[121,366,154], which is used for the controller 216 in the system 200. The function has a minimum value of 0.15, which means that the system 200 is capable of filtering on average 80% of the input tremor disturbances/ unintentional muscle movements in the frequency range of 3-7 Hz.

As above described, the system and method in accordance with the present invention allow for a highly compact active cancellation approach that seeks to accommodate a user's tremor by allowing it to exist while cancelling its effects and stabilizing the position of the object. By implementing a motion-generating mechanism to provide the necessary forces and displacements for tremor cancellation and a control system and sensor topology to control this motion-generating mechanism, the system and method in accordance with the present invention achieve a more robust handheld form-factor with a significantly reduced size and cost.

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A handheld system, comprising:
   a housing shaped for holding by a hand, the housing including an open end;
   a motion-generating mechanism at least partially disposed within the housing, the motion-generating mechanism including:
      a first motor mounted to the housing and adapted to generate a first rotary motion about a first axis; and
      a second motor mounted within the housing and coupled to a first output of the first motor such that the first rotary motion output from the first motor is imparted to the second motor and rotates the second motor relative to the housing within the housing, the second motor adapted to generate a second rotary motion about a second axis different from the first axis;
   an attachment arm extending through the open end of the housing and having first and second ends, the first end coupled to a second output of the second motor and the second end configured to attach a user assistive device, wherein the attachment arm is movable relative to the housing in two degrees of freedom;
   a motion sensor adapted to sense a motion of the handheld system and generate a feedback signal in response to the motion; and
   a control system disposed within the housing and coupled to the motion sensor to receive the feedback signal from the motion sensor, the control system further coupled to the motion-generating mechanism and configured to control the first and second rotary motions with commands generated based at least in part upon the feedback signal from the motion sensor, wherein the commands direct the motion-generating mechanism to move the attachment arm relative to the housing to stabilize the attachment arm from unintentional muscle movements of the housing.

2. The handheld system of claim 1, wherein the motion-generating mechanism further comprises:
   a first bearing supporting a first connection between the second motor and the first output of the first motor; and
   a second bearing supporting a second connection between the first end of the attachment arm and the second output of the second motor,
   wherein the first and second bearings are substantially orthogonal to each other.

3. The handheld system of claim 1, wherein the motion-generating mechanism further comprises:
   a first gear reduction system coupled to the first output of the first motor; and
   a second gear reduction system coupled to the second output of the second motor.

4. The handheld system of claim 1, wherein the motion sensor is disposed within the housing.

5. The handheld system of claim 4, wherein the motion sensor comprises a relative-motion sensor mounted within the housing to sense a relative motion between the housing and the attachment arm.

6. The handheld system of claim 5, wherein the relative-motion sensor comprises a contactless magnetic sensor.

7. The handheld system of claim 1, wherein the motion sensor comprises an absolute-motion sensor attached directly to the attachment arm between the first and second ends to sense an absolute motion of the attachment arm.

8. The handheld system of claim 7, wherein the absolute-motion sensor comprises an inertial sensor.

9. The handheld system of claim 7, further comprising:
   a relative-motion sensor mounted within the housing to sense a relative motion between the housing and the attachment arm, wherein the control system is configured to generate the commands for stabilizing the unintentional muscle movements based upon feedback from the absolute-motion sensor and the relative-motion sensor.

10. The handheld system of claim 1, wherein the user-assistive device comprises any of a kitchen utensil or a grooming utensil.

11. The handheld system of claim 1, wherein the attachment arm is configured to attach the user assistive device via a friction mechanism or a snap mechanism.

12. A handheld system, comprising:
    a housing shaped as a handle for holding;
    a motion-generating mechanism at least partially disposed within the housing, the motion-generating mechanism including:
       a first motor mounted to the housing and adapted to generate a first rotary motion; and
       a second motor coupled to a first output of the first motor such that the first rotary motion output from the first motor is imparted to the second motor and rotates the second motor relative to the housing within the housing, the second motor adapted to generate a second rotary motion;
    an attachment arm extending out of the housing and having first and second ends, the first end coupled to a second output of the second motor and the second end configured to attach a user assistive device;
    an absolute-motion sensor disposed directly on the attachment arm between the first and second ends and adapted to sense an absolute motion of the attachment arm and to generate a first signal in response; and a control system disposed within the housing and coupled to the absolute-motion sensor to receive the first signal, the control system further coupled to the motion-generating mechanism and configured to control the first and second rotary motions with commands generated based at least in part upon the first signal, wherein the commands direct the motion-generating mechanism to move the attachment arm relative to the housing to stabilize the attachment arm from unintentional muscle movements of the housing.

13. The handheld system of claim 12, wherein the motion-generating mechanism further comprises:
   a first bearing supporting a first connection between the second motor and the first output of the first motor; and
   a second bearing supporting a second connection between the first end of the attachment arm and the second output of the second motor,
   wherein the first and second bearings are substantially orthogonal to each other.

14. The handheld system of claim 12, wherein the motion-generating mechanism further comprises:
   a first gear reduction system coupled to the first output of the first motor; and
   a second gear reduction system coupled to the second output of the second motor.

15. The handheld system of claim 12, further comprising:
   a relative-motion sensor disposed in the housing to measure a relative motion between the housing and the attachment arm and to generate a second signal in response,
   wherein the control system is further coupled to the relative-motion sensor to receive the second signal and configured to control the first and second rotary motions with the commands generated based at least in part upon the first signal and the second signal.

16. The handheld system of claim 15, wherein the relative-motion sensor comprises a contactless magnetic sensor.

17. The handheld system of claim 12, wherein the user-assistive device comprises any of a kitchen utensil or a grooming utensil.

18. The handheld system of claim 12, wherein the attachment arm is configured to attach the user assistive device via a friction mechanism or a snap mechanism.

19. A handheld system for stabilizing human tremors, comprising:
   a housing;
   a motion-generating mechanism at least partially disposed within the housing, the motion-generating mechanism including:
      a first motor mounted to the housing and adapted to generate a first rotary motion; and
      a second motor coupled to a first output of the first motor such that the first rotary motion output from the first motor is imparted to the second motor and rotates the second motor relative to the housing within the housing, the second motor adapted to generate a second rotary motion;
   an attachment arm extending out of the housing and having first and second ends, the first end coupled to a second output of the second motor within the housing and the second end attached to a user assistive device;
   a motion sensor disposed within the housing and adapted to sense a motion of the handheld system and to generate a first signal in response to the motion; and
   a control system disposed within the housing and coupled to the motion sensor to receive the first signal, the control system further coupled to the motion-generating mechanism and configured to control the first and second rotary motions with commands generated based at least in part upon the first signal, wherein the commands direct the motion-generating mechanism to move the attachment arm relative to the housing to stabilize the user assistive device from the human tremors of the housing.

20. The handheld system of claim 19, wherein the motion-generating mechanism further comprises:
   a first bearing supporting a first connection between the second motor and the first output of the first motor; and
   a second bearing supporting a second connection between the first end of the attachment arm and the second output of the second motor,
   wherein the first and second bearings are substantially orthogonal to each other.

* * * * *